(12) United States Patent
Di Caprio et al.

(10) Patent No.: US 6,689,119 B1
(45) Date of Patent: Feb. 10, 2004

(54) SELF-ALIGNING MEDICAL DEVICE (75) Inventors: Fernando Di Caprio, Mendota Heights, MN (US); Brett Allyn Williams, Lino Lakes, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 178 days.

(21) Appl. No.: 09/586,102

(22) Filed: Jun. 2, 2000

(51) Int. Cl.$^7$ .................... A61M 25/00; A61M 5/00
(52) U.S. Cl. ................ 604/523; 606/194; 600/585
(58) Field of Search ................ 604/523, 264, 604/529, 528, 96.01, 93.01; 606/194, 585

(56) References Cited

U.S. PATENT DOCUMENTS

| | | | |
|---|---|---|---|
| 5,542,938 A | 8/1996 | Avellanet et al. | 604/280 |
| 5,606,980 A | 3/1997 | Calhoun et al. | 128/772 |
| 5,706,827 A | 1/1998 | Ehr et al. | 128/772 |
| 5,776,080 A | 7/1998 | Thome et al. | 600/585 |
| 5,931,818 A | 8/1999 | Werp et al. | 604/270 |
| 6,013,038 A | 1/2000 | Pflueger | 600/585 |

FOREIGN PATENT DOCUMENTS

| | | | | |
|---|---|---|---|---|
| WO | PCT/US95/01857 | * | 8/1995 | A61B/5/00 |
| WO | WO 95/21566 | | 8/1995 | |
| WO | WO 99/42167 | | 8/1999 | |

* cited by examiner

Primary Examiner—Brian L. Casler
Assistant Examiner—Matthew F. DeSanto
(74) Attorney, Agent, or Firm—Westman, Champlin & Kelly, P.A.

(57) ABSTRACT

A self-centering or alignment system for catheter or other medical treatment devices. The system includes magnets on interacting elongate devices to separate and align the elongate devices for use. The interactive elongate devices can include a guide catheter and treatment catheter or a treatment catheter and guide wire. The system of the present invention facilitates insertion and placement of medical devices at a treatment site and provides enhanced maneuverability and insertability for treatment devices.

22 Claims, 7 Drawing Sheets

SELF-ALIGNING MEDICAL DEVICE

BACKGROUND OF THE INVENTION

The present invention relates to improved deliverability of implantable devices or devices inserted into a body tract or a body cavity of a patient. In particular, the present invention relates to a self-centering or self-aligning implantable device.

Various types of catheters are known for treating cardiac or other disorders. Catheters are temporarily inserted into the vascular system, the urinary tract, or other such tracts. Catheter devices include an elongated shaft having sufficient length to track from an insertion position to a remote treatment site in a body vessel. Catheter devices are externally manipulated and maneuvered to reach a remote site. The tortuous profile of a body vessel increases the difficulty of externally manipulating the catheter to a remote treatment site. It is therefore desirable that the shaft supporting the catheter have sufficient rigidity for pushabality and torqueability to facilitate external manipulation of the catheter and sufficient flexibility to enable tracking of bends and contours of the body vessel.

Catheters used to treat coronary heart disease are typically tracked from a femoral or brachial insertion point through a patient's vasculature to a coronary treatment site. The treatment catheter can be inserted through a guide catheter or advanced along a guide wire. The guide catheter can be pre-shaped or bent to conform to the vessel contour to facilitate insertion and placement in the treatment vessel. The distal end of the treatment catheter is steered through the guide catheter by the application of torque and force which is transmitted from a proximal end of the catheter that resides outside the patient. The treatment catheter is also steered, in part, through engagement or contact between the treatment catheter and the guide catheter walls. Manipulating or steering the catheter along the insertion path through contact with the guide catheter increases operating friction, retards advancement of the treatment catheter and can kink or damage a tip or body of the treatment catheter.

If the treatment catheter is positioned with a guide wire, the treatment catheter typically includes a guide wire lumen in the catheter shaft which receives the guide wire. The guide wire includes a lower profile than the catheter shaft and can be independently advanced to a treatment site or stenosis. Thereafter, the treatment catheter which may be preloaded on the guide wire is advanced along the guide wire to position the catheter at the treatment site. The treatment catheter can also be after loaded onto a pre-inserted guide wire to accomplish a catheter exchange. Friction and contact between the walls of the guide wire lumen in the catheter shaft and the guide wire can impede or restrict advancement of the treatment catheter over the guide wire. The present invention addresses these and other problems.

SUMMARY OF THE INVENTION

The present invention relates to a self-centering or alignment system for a catheter or other treatment device. The system includes magnets on interacting elongate devices to separate and align the elongate devices for use. The interactive elongate devices can include a guide catheter and the treatment catheter. The interactive elongate devices can also include a treatment catheter and guide wire for advancing or tracking the treatment catheter over the guide wire. The system of the present invention facilitates insertion and placement of medical devices at a treatment site and provides enhanced maneuverability and insertability for treatment devices.

DETAILED DESCRIPTION OF THE PREFERRED EMBODIMENTS

Figure 1:
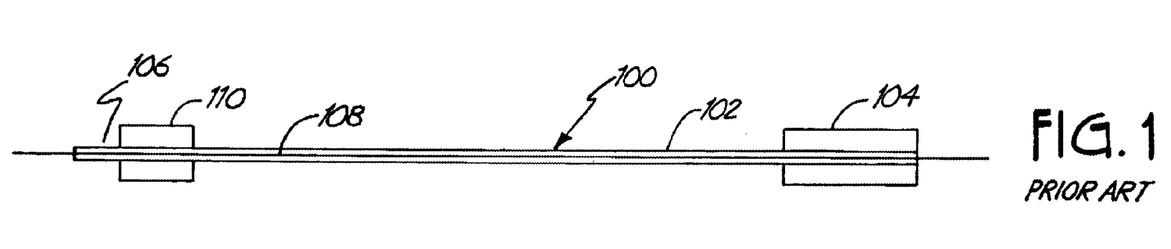
FIG. 1 illustrates an embodiment of a treatment catheter having a guide wire.

FIG. 1 illustrates an elongated treatment catheter 100 having an elongated flexible catheter shaft 102. Catheter shaft 102 includes proximal and distal ends 104, 106. The treatment catheter 100 in the embodiment shown is an over-the-wire catheter having a guide wire 108 extending through a lumen along the catheter shaft 102. The treatment catheter illustrated is, by way of example only, a dilatation catheter and includes a dilatation balloon 110 at the distal end 106. Dilatation balloon 110 is inflated or deflated to dilate a lesion or stenosis as is known. Although a dilatation catheter is shown, it should be understood that catheter 100 is not limited to a dilatation catheter or the particular over-the-wire catheter shown and can include other treatment catheters including radiation catheters, rapid exchange or fixed wire catheters, drug delivery or stent delivery catheters, perfusion catheters, drainage catheters or other such implantable medical devices.

Figure 2A:
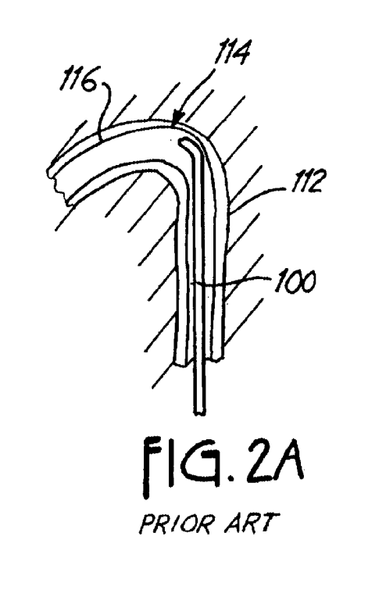
FIGS. 2A–2C progressively illustrate insertion of a treatment catheter through a guide catheter.
Figure 2B:
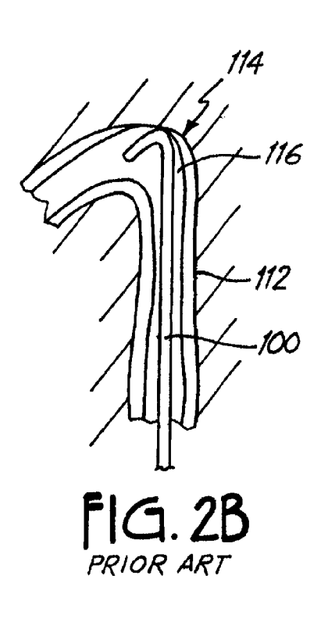
Figure 2C:
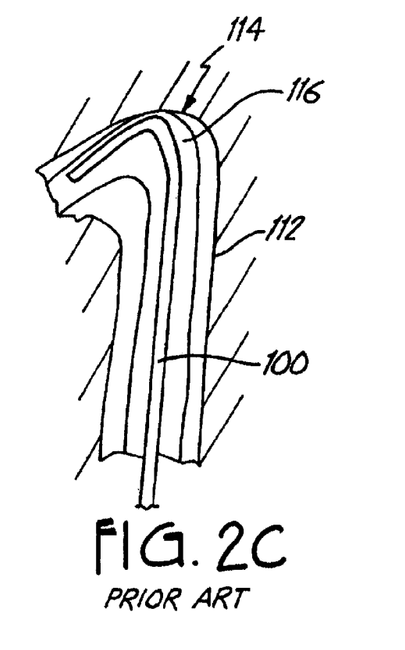

As previously explained, catheters are advanced within a body cavity or vessel to a treatment site. For insertion, the catheter has to bend or curve to follow a tortuous body lumen or vessel to a treatment site. FIGS. 2A–2C illustrate a vessel 112 to be treated including a curved vessel contour 114 around which the catheter must track. Typically, catheter 100 may be inserted through a preinserted guide catheter 116. The catheter 100 is externally steered from the proximal end of the catheter shaft through the guide catheter 116 to a treatment site (not shown) located proximate the distal end of the guide catheters. As progressively shown in FIGS. 2A–2C, catheter 100 is steered in part through contact with the guide catheter 116. Tracking the catheter along the guide catheter 116 through contact with the guide catheter walls can increase operating friction and slow or impede insertion of the catheter 100 to the treatment site.

Figure 3:
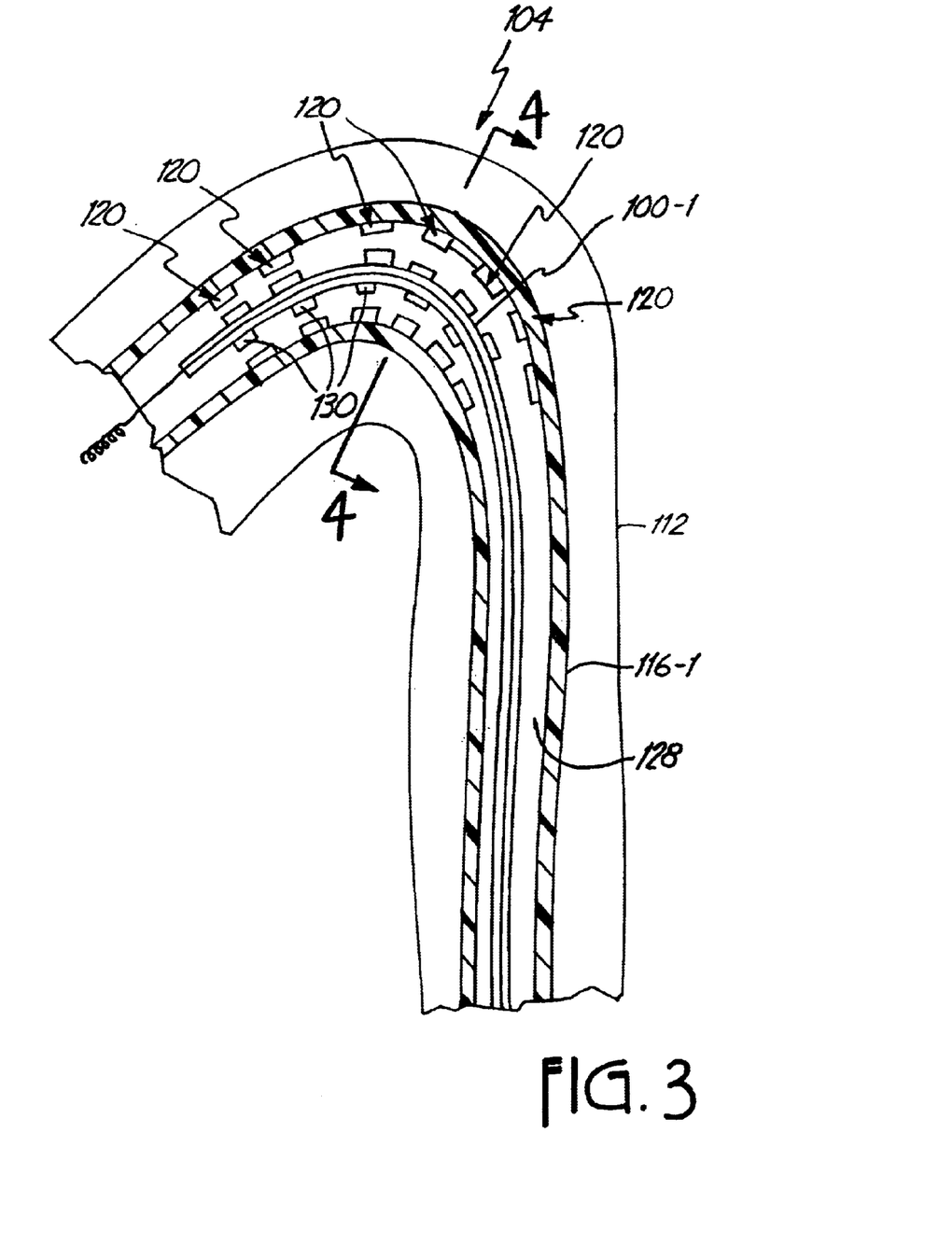
FIG. 3 illustrates an embodiment of a self-aligning system for a guide catheter and treatment catheter.
Figure 4:
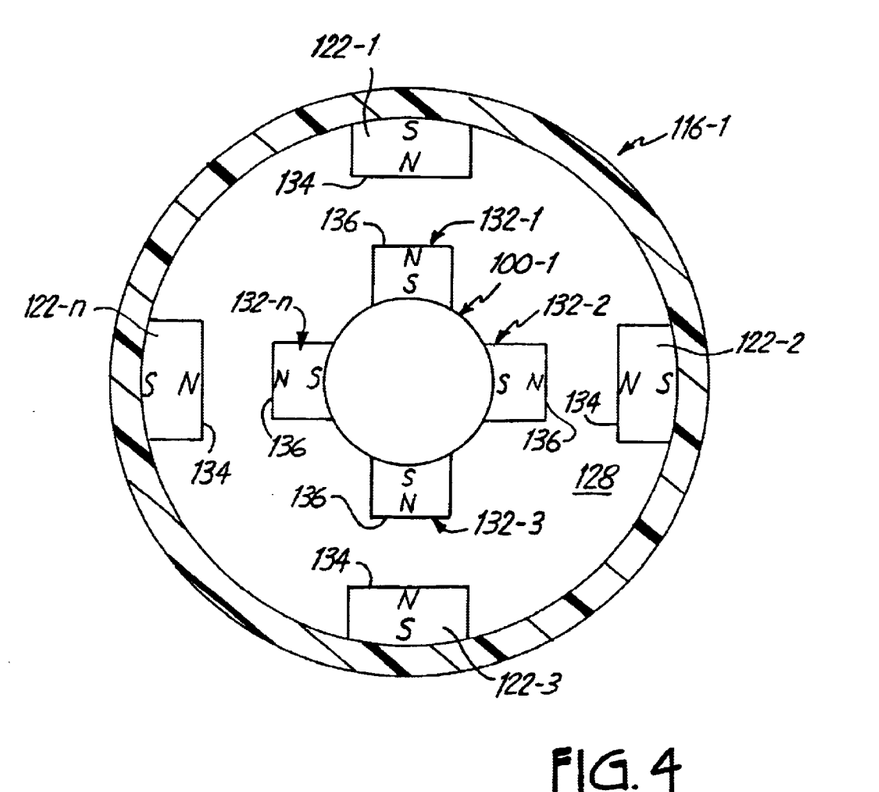
FIG. 4 is a cross-sectional view taken along line 4—4 of FIG. 3.

The present invention includes a self centering catheter system for imparting an external steering force on a treatment catheter 100-1 through a guide catheter 116-1 which is schematically illustrated in FIGS. 3–4. As shown, guide catheter 116-1 includes a plurality of longitudinally spaced magnets 120 along a portion of the length thereof. FIG. 4 shows that the longitudinally spaced magnets 120 include radially spaced magnet segments 122-1 through 122-n (collectively referred to as segments 122) extending about a circumference of the guide catheter 116-1. As will be discussed in greater detail with respect to FIG. 7B below, magnets 120 (and magnets 130 discussed below) can be annular rings as well, but the present discussion continues with respect to radially spaced segments. Radially spaced magnet segments 122 are aligned so that the magnetic poles (north and south) of each of magnet segments 122 face radially inwardly and radially outwardly, respectively. Each of the radially inwardly facing poles extending about the circumference of the guide catheter 116-1 and facing inward toward guide catheter lumen 128 has a common polarity.

Treatment catheter 100-1 includes distal magnets 130 illustrated diagrammatically. Distal magnets 130 include a plurality of radially spaced magnet segments 132-1 through 132-n (collectively referred to as segments 132) as shown in FIG. 4. Radially spaced magnet segments 132 are aligned so that the magnet poles (south and north) of each of the magnet segments 132 face radially inwardly and radially outwardly, respectively. Each of the radially outwardly facing poles extending about the circumference of the catheter 100-1 has a common polarity. The radially inwardly facing poles on catheter 116-1 and radially outwardly facing poles on the catheter 100-1 form opposed poles 134, 146, respectively, on guide catheter 116-1 and treatment catheter 100-1. Because the polarity of the opposed poles 134, 136 is similar, the magnet segments or poles repel one another to maintain separation between catheters 100-1 and 116-1 and to center the treatment catheter. 100-1 relative to the guide catheter 116-1 between the walls of guide catheter 116-1, as will be explained.

As the catheter 100-1 is distally advanced through guide catheter 116-1 for placement at a treatment site, the interaction between the opposed poles of magnet segments 122 and 132 directs the catheter 100-1 through the guide catheter 116-1 and around curved or contoured portions of the guide catheter 116-1. In particular the magnets 130 at the distal end 106 of the catheter repel the treatment catheter from the walls of guide catheter via opposed pole forces of the active magnets on the treatment catheter and guide catheter so the treatment catheter tracks the treatment site without significant contact interface between the guide catheter 116-1 and treatment catheter 100-1.

Although a particular pole designation for magnet segments 122, 132 is shown, thus application is not limited to the particular pole orientation shown and can include other pole orientations to track the catheter 100-1 through the guide catheter 116-1. Also, in the embodiment shown, magnets 120 extend along a curved portion of the guide catheter 116-1 for directing the distal end 106 of the treatment catheter around a curved portion of the guide catheter 116-1. However, in one embodiment, the pitch and spacing between magnets can be varied based on the curvature of the catheter device for providing desired alignment or centering of the treatment catheter within the guide catheters. In another embodiment, magnets can extend along a longer portion, or the entire length, of the guide catheter 116-1. Further, catheter 100-1 includes at least one magnet 130 at the distal end of the catheter for tracking the distal end of the catheter through the guide catheter 116-1. Alternatively, multiple magnets 130 can be spaced along a portion of, or the entire length of, the treatment catheter shaft.

The magnets used herein are illustratively active magnets which produce a magnetic field and can be permanent magnets or electromagnetic elements coupled to an external power source. The magnets can also be formed of a magnetized coil. Further, separate magnet segments can be coupled to respective catheter walls or can be formed integral with the material of the catheter shaft. For example, the magnet segments can be attached to inner or outer surfaces of the catheter shaft or embedded in the catheter shaft between the inner and outer surfaces.

Figure 5:
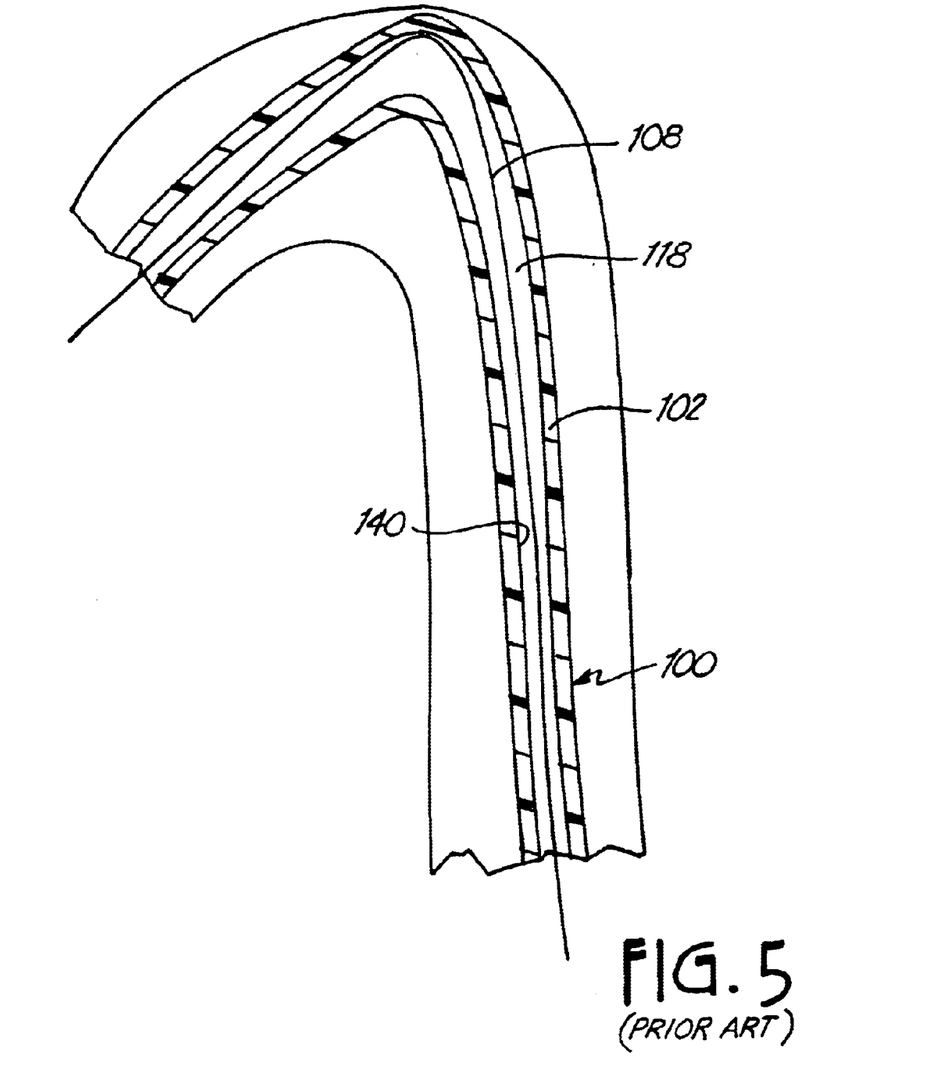
FIG. 5 illustrates a portion of a catheter having a guide wire extending therethrough inserted into a body vessel for treatment.

As previously discussed, and as shown in FIG. 5, a treatment catheter 100 can also be advanced over a guide wire 108 to a treatment site. Friction and contact between a guide wire 108 and catheter shaft 102 can restrict or impede independent movement of catheter shaft 102 over the guide wire 108 for placement at a treatment site. As shown, in FIG. 5, guide wire 108 is formed of a flexible material which bends or curves to follow a vessel contour. The bent or curved portions of the guide wire can abut against a vessel wall or the guide wire lumen walls in catheter shaft 102, which inhibits movement of the catheter shaft 102, along the guide wire and increases friction between the catheter shaft 102 and guide wire 108.

Figure 6:
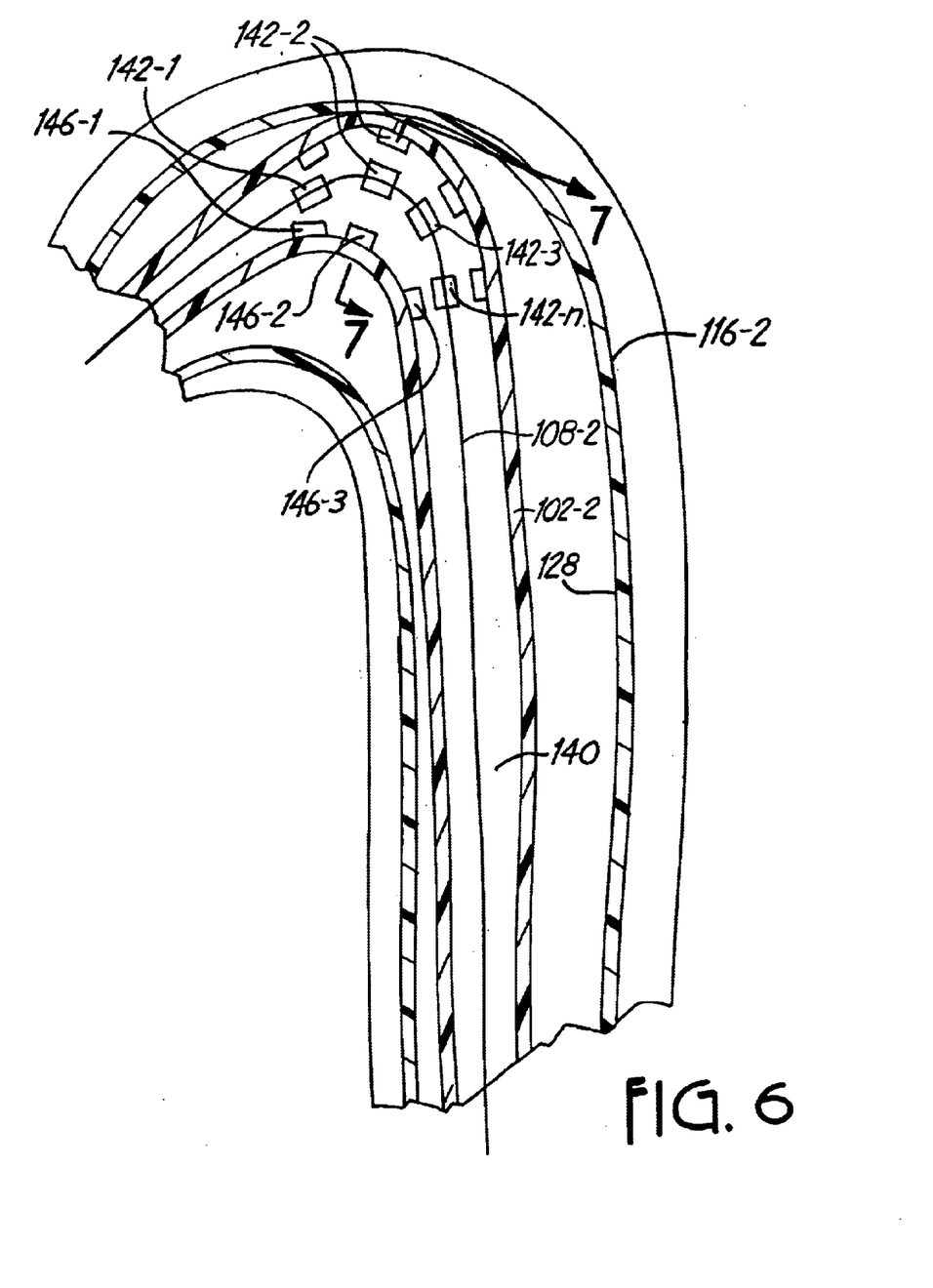
FIG. 6 illustrates an embodiment of a self aligning system for a catheter and guide wire.
Figure 7A:
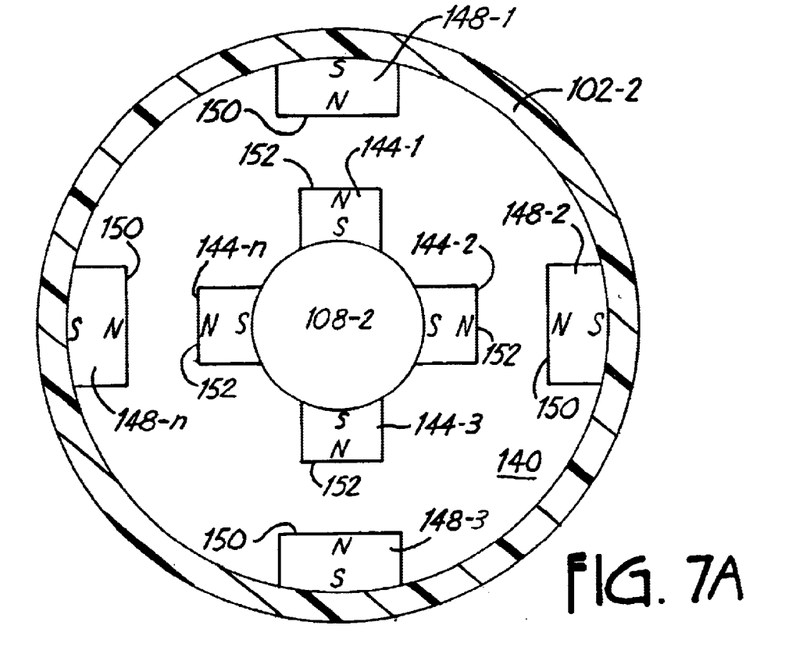
FIGS. 7A and 7B are two embodiments of cross-section views taken along lines 7—7 of FIG. 6.

FIGS. 6–7A illustrate an embodiment of a self alignment system for a catheter shaft 102-2 and guide wire 108-2. It should be noted that the guide wire can either be hollow or solid core. As shown, guide wire 108-2 includes a plurality of longitudinally spaced magnets 142-1 through 142-n (collectively referred to as magnets 142) along a length of the guide wire 108-2. Each magnet 142 includes a plurality of radially spaced magnet segments 144-1 through 144-n (collectively referred to as segments 144). Radially spaced magnet segments 144 are aligned so that opposed magnetic poles (north and south) of each of the magnet segments 144 face radially inwardly and radially outwardly, respectively. Thus, each of the radially outwardly facing poles extending about the circumference of the guide wire 108-2 has a common polarity facing radially outwardly towards the catheter shaft 102-2.

Catheter shaft 102-2 also includes a plurality of longitudinally spaced magnets 146-1 to 146-n (collectively referred to as magnets 146). Magnets 146 on catheter shaft 102-2 include a plurality of radially spaced magnet segments 148-1 through 148-n (collectively referred to as segments 148) as shown in FIG. 7. Radially spaced magnet segments 148 are aligned so that the magnetic poles (south and north) of each of the magnet segments 148 face radially inwardly and radially outwardly, respectively. Thus, each of the radially outwardly facing poles extending about the circumference of the guide wire 108-2 has a common polarity to the magnetic segments 144 facing radially inwardly towards the guide wire 108-2 from the catheter shaft 102-2.

The radially inwardly facing poles on catheter shaft 102-2 and radially outwardly facing poles on the guide wire 108-2 form opposed poles 150, 152 on catheter shaft 102-2 and guide wire 108-2. The polarity of the opposed poles 150, 152 is similar so that the magnet segments or poles repel one another to maintain separation between guide wire 108-2 and the walls of the guide wire lumen in treatment catheter shaft 102-2. In the embodiment shown, magnet segments 144, 148 are located towards a distal portion of guide wire 108-2 and catheter shaft 102-2 to provide alignment for curved or bent portions of the catheter system. However, magnet segments 144, 148 can be located along any portion or interval of the guide wire 108-2 or catheter shaft 102-2 to provide separation and alignment for the catheter shaft along the guide wire. Similarly, the spacing between the magnets or magnet segments can be uniform or varied to achieve higher magnetic fields along curved positions of the catheter system, or otherwise, as desired.

Figure 7B:
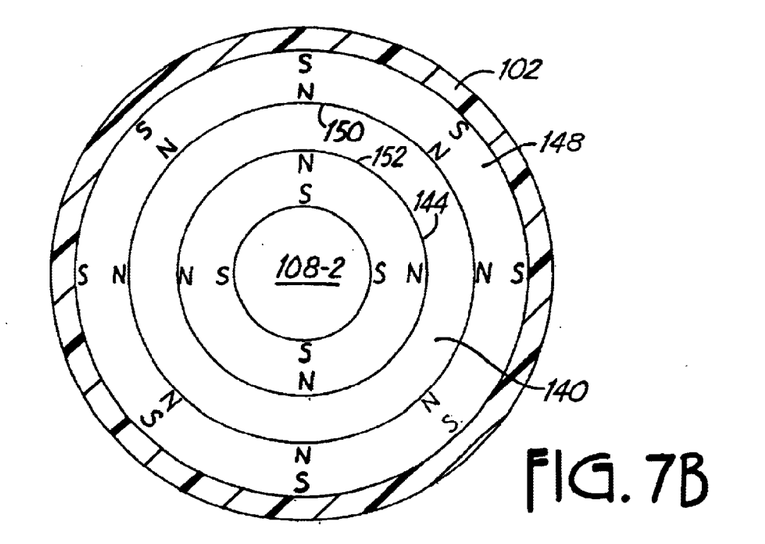

FIG. 7B illustrates another embodiment of the present invention which is similar to that shown in FIG. 7A, but segments 144 and 148 have been replaced by a plurality of longitudinally spaced magnetic annular rings. The embodiment operates in substantially the same manner as that shown in FIGS. 4 and 7A.

Also, as previously discussed, magnet segments 144, 148 are illustratively magnets which produce a magnetic field and can be permanent magnets or electromagnets which are activated via an external power source. The active magnets are adhered to or embedded into the catheter shaft 102-2 and guide wire 108-2 and application of the present invention is not limited to any particular magnet structure. Thus, as described, guide wire 108-2 is centered along catheter shaft 102-2 so that the catheter shaft 102-2 can be freely advanced over the guide wire 108-2 without significant interference.

Figure 8:
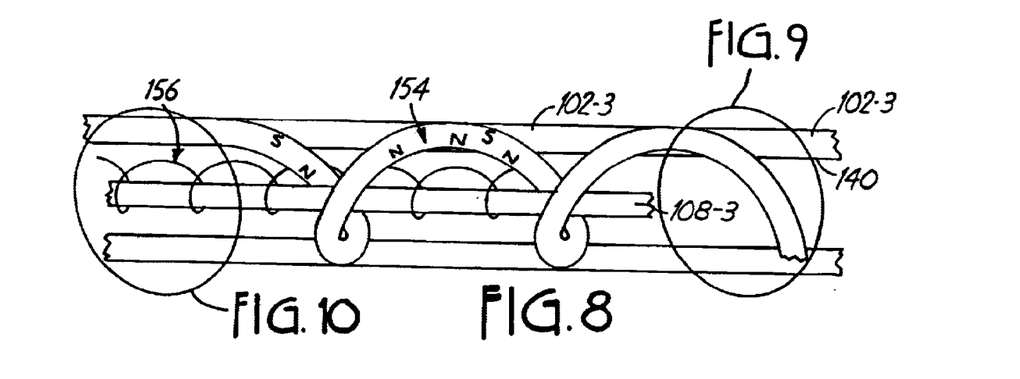
FIG. 8 illustrates an embodiment of a self aligning system for a catheter and guide wire.
Figure 9:
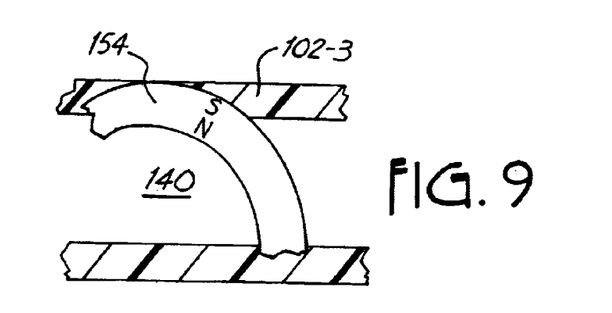
FIG. 9 is a detailed view of portion 9 of FIG. 8.
Figure 10:
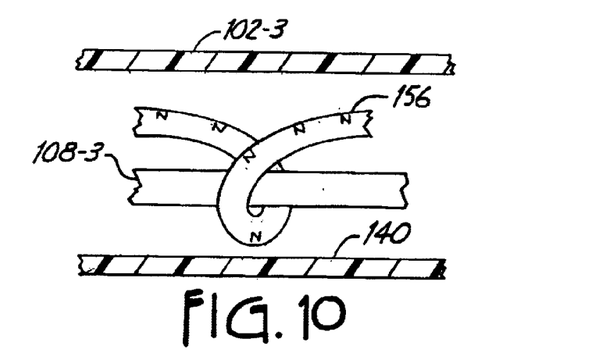
FIG. 10 is a detailed view of portion 10 of FIG. 8.

FIGS. 8–10 illustrate alternate embodiments for aligning or centering a catheter shaft 102-3 and a guide wire 108-3 extending through a lumen in the catheter shaft. Catheter shaft 102-3 includes a magnetized coil 154 wrapped around a circumference of the catheter shaft 102-3. The magnetized coil 154 is formed of a magnetized wire, as better illustrated in FIG. 9, which is wrapped about the catheter, or embedded in the catheter wall, so that a common pole faces radially inwardly towards the guide wire lumen 140. Guide wire 108-3 includes a magnetized coil 156 wrapped about a circumference of the guide wire 108-3. The coil 156 is formed of a magnetized wire, as better illustrated in FIG. 10, which is wrapped about wire 108-3 (or embedded therein) so that a common pole faces radially outwardly. Inward pole of coil 154 and outward pole of coil 156 have similar polarity to maintain separation between the catheter 102-3 and guide wire 108-3 via interaction between opposed pole forces of the magnetized coils 154, 156. Although a particular polarity is shown, the application is not limited to the particular polarity or orientation shown.

The length of the magnetized coils 154, 156 can extend along portions of the catheter shaft 102-3 and guide wire 108-3 or along the length of the catheter shaft 102-3 or guide wire 108-3 between the proximal and distal ends of the shaft 102-3 or guide wire 108-3. Alternatively, a plurality of magnetized wire segments can be used to form magnetized coils 154, 156 along the length of the catheter shaft 102-3 or guide wire 108-3 or portion thereof. For use, the magnetizable coil 154 can be embedded into and formed with the catheter shaft 102-3 or coupled to an inner or outer surface of the catheter shaft 102-3. Similarly, the pitch of the coils can be varied along the longitudinal length of the coil to increase or decrease coil density (i.e., increase or decrease the number of turns per unit length) to vary the strength of the magnetic field generated at different positions along the coil, as desired.

The aligning or centering systems use opposed repulsion forces or opposed active magnets to maintain separation between interacting treatment devices to reduce friction, and improve tractability, external steerability and maneuverability of the treatment apparatus. As described, the term centering refers to the process of separating devices using opposed active magnets so that the devices do not contact one another (or so that contact is reduced or controlled) and use of the term is not limited to an exact centered relationship between interactive devices. Application of the aligning system shown is not limited to balloon catheters but could be used for stent delivery systems, radiation catheters, or any other catheters.

Although the present invention has been described with reference to preferred embodiments, workers skilled in the art will recognize that changes may be made in form and detail without departing from the spirit and scope of the invention.

What is claimed is:

1. A catheter system, comprising:
    a first elongate body configured for insertion into a body lumen having a longitudinal dimension along an elongate length and a radial dimension; and
    a second elongate body configured for insertion through a lumen of the first elongate body having a longitudinal dimension along an elongate length and a radial dimension;
    a magnet assembly coupled to the first and second elongate bodies and having a polarity to provide a radial centering force between the first and second elongate bodies in a radial direction.

2. The catheter system of claim 1 wherein the first elongate body comprises:
    an elongated flexible guide catheter and the second elongate body includes a treatment catheter having an elongate shaft sized to be received within the lumen of the guide catheter.

3. The catheter system of claim 2 wherein magnet assembly includes a guide catheter magnet and a treatment catheter magnet having a repulsive polarity about the radial dimension of the treatment catheter and the radial dimension of the guide catheter to provide the radial centering force between the guide catheter and the treatment catheter.

4. The catheter system of claim 3 wherein the guide catheter includes a plurality of longitudinally spaced magnets along the elongated length thereof.

5. The catheter system of claim 4 wherein the plurality of longitudinally spaced magnets are comprised of windings of a magnetized coil coupled to the guide catheter.

6. The catheter system of claim 3 wherein the treatment catheter includes a plurality of magnets longitudinally spaced along the elongated length thereof.

7. The catheter system of claim 6 wherein the plurality of longitudinally spaced magnets are comprised of windings of a magnetized coil coupled to the treatment catheter.

8. The catheter system of claim 2 wherein the magnet assembly includes a guide catheter magnet and a treatment catheter magnet wherein the guide catheter magnet and the treatment catheter magnet include opposed radially inward and radially outward poles and the radial inward pole of the guide catheter magnet and the radial outward pole of the treatment catheter magnet have the same polarity to provide the radial centering force between the guide catheter and the treatment catheter.

9. The catheter system of claim 1 wherein the second elongate body comprises:
    an elongate flexible guide wire and the first elongate body comprises a treatment catheter and the guidewire extends through the lumen of the treatment catheter.

10. The catheter system of claim 9 wherein the magnet assembly includes a treatment catheter magnet and a guide wire magnet having a repulsive polarity about the radial dimension of the guidewire and the radial dimension of the treatment catheter to provide the radial centering force between the guide wire and the treatment catheter.

11. The catheter system of claim 10 wherein the treatment catheter magnet includes a magnetized coil coupled to the treatment catheter.

12. The catheter system of claim 10 wherein the treatment catheter magnet includes a plurality of magnets longitudinally spaced along the elongate length of the treatment catheter.

13. The catheter system of claim 10 wherein the guide wire magnet comprises a magnetized coil coupled to the guide wire.

14. The catheter system of claim 10 wherein the guide wire magnet comprises a plurality of longitudinally spaced magnets coupled to the guide wire.

15. The catheter system of claim 9 wherein the magnet assembly includes a treatment catheter magnet and a guide wire magnet and the treatment catheter magnet and the guide wire magnet include opposed radially inward and radially outward poles and the radial inward pole of the treatment catheter magnet and the radial outward pole of the guidewire magnet have the same polarity to provide the radial centering force between the treatment catheter and the guide wire.

16. A method of treating a body vessel with an insertable catheter device comprising steps of:

inserting an elongate member into the body vessel including a magnet;

inserting a treatment catheter, having a magnet, along the elongate member; and radially centering the treatment catheter relative to the elongate member by interaction of magnetic fields provided by the magnet on the elongate member and the magnet on the treatment catheter.

17. The method of claim 16 wherein the elongate member comprises a guide catheter and wherein the treatment catheter is radially centered by mutual repulsion of the magnets on the guide catheter and the treatment catheter.

18. The method of claim 16 wherein the elongate member comprises a guide wire and wherein the treatment catheter is radially centered by mutual repulsion of the magnets on the treatment catheter and the guide wire.

19. A catheter system comprising:

first and second flexible elongate members configured for insertion into a body lumen having a longitudinal dimension and a radial dimension; and radial centering means coupled to the first and second elongate members, for radially centering the first and second elongate members relative to one another.

20. The catheter system of claim 19 wherein the first and second elongate members comprise a guide catheter and a treatment catheter, respectively.

21. The catheter system of claim 20 wherein the first and second elongate members comprise a treatment catheter and a guide wire, respectively.

22. The catheter system of claim 19 wherein the radial centering means comprises:

a first magnet on the first elongate member; and a second magnet on the second elongate member, the first and second magnets having a repulsive polarity in a radial direction to exert a centering force on the first and second elongate members for radially centering the first and second elongate members.

* * * * *